United States Patent [19]

Baudin et al.

[11] Patent Number: 5,416,027
[45] Date of Patent: May 16, 1995

[54] PROCESS AND APPARATUS FOR MONITORING THE PROGRESS OF HEMODIALYSIS

[75] Inventors: Serge Baudin, Herbault; Philippe Jussiaux, Chambly, both of France

[73] Assignee: Laboratoire Eugedia, Chambly, France

[21] Appl. No.: 1,721

[22] Filed: Jan. 7, 1993

[30] Foreign Application Priority Data

Jan. 7, 1992 [FR] France ................... 92 00063
Feb. 6, 1992 [FR] France ................... 92 01333

[51] Int. Cl.⁶ ............... G01N 33/86; G01N 27/28; B01D 11/00
[52] U.S. Cl. .................... 436/70; 73/61.41; 210/646; 324/450
[58] Field of Search .......... 436/55, 70; 73/61.41; 210/646; 324/450

[56] References Cited

U.S. PATENT DOCUMENTS

| | | | |
|---|---|---|---|
| 4,068,169 | 1/1978 | Angel et al. | 324/71 |
| 4,418,313 | 11/1983 | Cserey et al. | 324/71.1 |
| 4,437,469 | 3/1984 | Djordjevich et al. | 128/672 |
| 4,508,622 | 4/1985 | Polaschegg et al. | 210/96.2 |
| 4,547,735 | 10/1985 | Kiesewetter et al. | 324/450 |
| 4,562,843 | 1/1986 | Djordjevich et al. | 128/672 |
| 4,661,246 | 4/1987 | Ash | 210/87 |
| 4,939,925 | 7/1990 | Sakuma et al. | 73/61.4 |

FOREIGN PATENT DOCUMENTS

| | | |
|---|---|---|
| 0029793 | 6/1981 | European Pat. Off. |
| 0089003 | 9/1983 | European Pat. Off. |
| 0272414 | 6/1988 | European Pat. Off. |

*Primary Examiner*—Nina Bhat
*Attorney, Agent, or Firm*—Jacobson, Price, Holman & Stern

[57] ABSTRACT

A process and an apparatus for monitoring the progress of haemodialysis by extra-corporeal measurement of the haematocrit are presented. The process comprises the steps of:

calculating at a given time the variation of a function of the haematocrit over a short period, on the one hand, and over a medium period preceding this time, on the other, comparing the values of these variations, the result of this comparison is a first indicator of the progress of the haemodialysis.

18 Claims, 3 Drawing Sheets

PROCESS AND APPARATUS FOR MONITORING THE PROGRESS OF HEMODIALYSIS

FIELD OF THE INVENTION

The invention concerns the techniques for controlling haemodialysis (or hemodialysis) and, in particular, those using the measurement of the haematocrit (or hematocrit) of the patient's blood.

The haematocrit is the ratio of the volume occupied by the red blood cells to the whole blood volume.

In patients who are victims of renal insufficiency, use is made of the artificial kidney to purify their blood and to adjust the water volume of the organism to the desired value. The invention concerns in particular this second mechanism, in which use is made in the dialyzer of the phenomenon of ultrafiltration through a semipermeable membrane. During this operation, liquid is extracted from the patient's plasma, and the same plasma, in equilibrium with the interstitial tissue and the cells of the organism, extracts liquid from them in turn. If the operation is carried out too rapidly for the organism, a 'plasma hypovolaemia' appears. These are the mechanisms that the invention proposes to control.

The decrease in circulating blood volume (volaemia) during dialysis sessions, resulting from complex mechanisms of multi-compartmental exchanges, is one of the most important factors in the haemodynamic intolerance of this therapeutic method. After a latency phase of varying length, due to the implementation of the biological compensation mechanisms, this hypovolaemia often gives rise to clinical systems of cardiovascular collapse, sometimes benign, sometimes impressive, and even grave in fragile patients. Therapeutic means or preventive and/or curative techniques certainly exist. The problem is to determine exactly when and how to use them knowingly. It is well established, by cumulative experience and by already older work, that the discontinuous monitoring of the arterial blood pressure and of the heart beat rate, even very frequent, does not make it possible in many cases to detect incidents sufficiently early, due probably to the sudden character of the collapse of the compensation systems.

The invention aims to furnish a method for monitoring the progress of haemodialysis, which allows for fairly early prediction of a deficiency in the compensation of the hypovolaemia by the organism, in order to enable the observation personnel to act sufficiently early and thus to prevent any cardiovascular collapse. The method must be simple to implement, safe and non-traumatic for the patient.

DESCRIPTION OF THE PRIOR ART

Different methods have been proposed for monitoring the haematocrit during haemodialysis. Several use colorimetry to monitor directly the red blood count in the serum.

The continuous measurement of the impedance of the whole body has been used by several authors (Tender, de Vries, Scanferla) to monitor dialysis, with some success. However, the apparatus used is costly, bothers the patient, and demands relative immobility. The method is also unreliable, because the bioelectric properties of the cell membranes are often extremely disturbed in the dialyzed patient.

A method for measuring the circulating blood volume was proposed in European Patent No. EP-0.272.414.B, wherein it is proposed to apply complicated formulas including the conductivity of the fresh dialyzate, the blood rate, the power characteristics of the dialyzer, to determine first the conductivity of the plasma and that of the blood, and then, from these, to determine continuously the haematocrit, from which the volaemia is determined, making it possible to monitor the dialysis parameters. This method, which is highly complicated, demands many calibrations to be reliable. The standard formulas used in the calculations are not generally adapted to all patients. Methods of this type also leave little leeway for action by the practitioner, who nevertheless bears sole responsibility for the operations.

The method of the invention, by comparison, furnishes accurate details about the variation in the haematocrit. These enable the practitioner to predict, and accordingly to prevent the reactions of the patient's organism.

A combination method using both a measurement of the body impedance and a measurement of the blood impedance upstream from the haemodialysis apparatus was proposed in European Patent No. E.P.0.029.793.B. The first of these measurements is taken by implanting needles in a hand and a foot of the patient. These serve as electrodes for two currents, one at a frequency of 1 MHz and the second at 5 kHz. Thanks to these currents, two impedances are determined. A second pair of electrodes installed in the external blood circuit, upstream from the dialyzer, also allows an impedance measurement, 5 kHz here. A comparison of these three impedances enables the practitioner to monitor the progress of the dialysis. It is also proposed to set a bottom limit on the impedance measured on the external blood circuit. An alarm is triggered if this limit is reached. The apparatus, the object of Patent No. EP-0.029.793.B, enables the practitioner to monitor the progress of the haemodialysis. However, if it is to be used merely to relieve the practitioner from very close observation by using the alarm system connected to the threshold reached by the impedance of the external circuit, it is first necessary to calibrate it for each patient. It has also been proved that this limit threshold is reached very late, practically at the same time that the decrease in the arterial blood pressure itself can be detected.

Furthermore, the method of Patent No. EP-0.029.793.B causes the patient, already traumatized by the haemodialysis, to submit to additional needles, which it would be preferable to avoid.

The two preceding techniques have the common drawback of combining the results of several measurements by calculation. These measurements, like all biological measurements, have their range of uncertainty. Introducing them into complicated calculations incurs the risk of cumulating these errors and of reaching false conclusions, which is liable to complicate the practitioner's job of observation.

Given the above mentioned definition of the haematocrit, its measurement can be obtained by measuring the red blood count or by measuring the plasma volume. The electronic systems associated with the sensors perform the necessary conversions. This is why, in the following discussion, the term haematocrit denotes either the actual haematocrit, or the red blood count (erythrocytes) or the plasma volume.

SUMMARY OF THE INVENTION

The invention concerns a process for monitoring the progress of haemodialysis by extra-corporeal measurement of the haematocrit, which requires:

calculating at a given time the variation of a function of the haematocrit over a short period, on the one hand, and over a medium period preceding this time, on the other, comparing the values of these variations, the result of this comparison is a first indicator of the progress of the haemodialysis.

If the short-term variation is greater than the medium-term variation, the indicator increases the value that it indicates, and it decreases this value when the short-term variation is less than the medium-term variation. Advantageously, the medium-term variation is about three times the short-term variation, and preferably about 15 min, and the combination of the first and second indicators of the progress of haemodialysis constitutes the alarm level. Preferably, the measurement of the haematocrit results from a measurement of the blood impedance, and the impedance measured is the result of average instantaneous measurements preferably taken at a frequency of 5 kHz.

The invention also concerns the apparatus that allows the implementation of the process and which comprises a measurement cell designed to be placed in a haemodialysis circuit, a constant-current generator, an impedance meter, said measurement cell comprising a semi-rigid tube provided with two openings closed by caps and each connected to the current source, on the one hand, and to the impedance meter on the other, and which comprises a calculator receiving the signal generated by the impedance meter and actuating a haemodialysis progress indicator.

The essential advantage of the method and of the device of the invention is to allow the early detection of hypovolaemia, long before any traumatizing manifestation, and thus to protect the patient from any risk of collapse.

The simplicity of the method allows the construction of uncomplicated and hence relatively cheap instruments, thus facilitating their widespread use.

Computer processing of the results enables their convenient use for medical research.

BRIEF DESCRIPTION OF THE DRAWINGS

The description and the figures that follow allow an understanding of the operation of the invention and the appreciation of its advantages.

Figure 4:
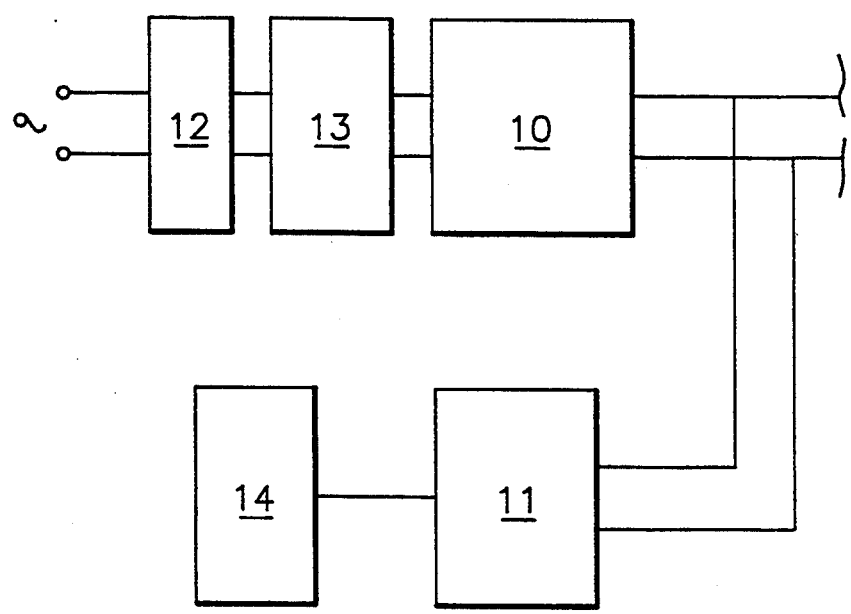

As to FIG. 4, it shows the functional diagram of the series of operations performed by the device of the invention.

Figure 5:
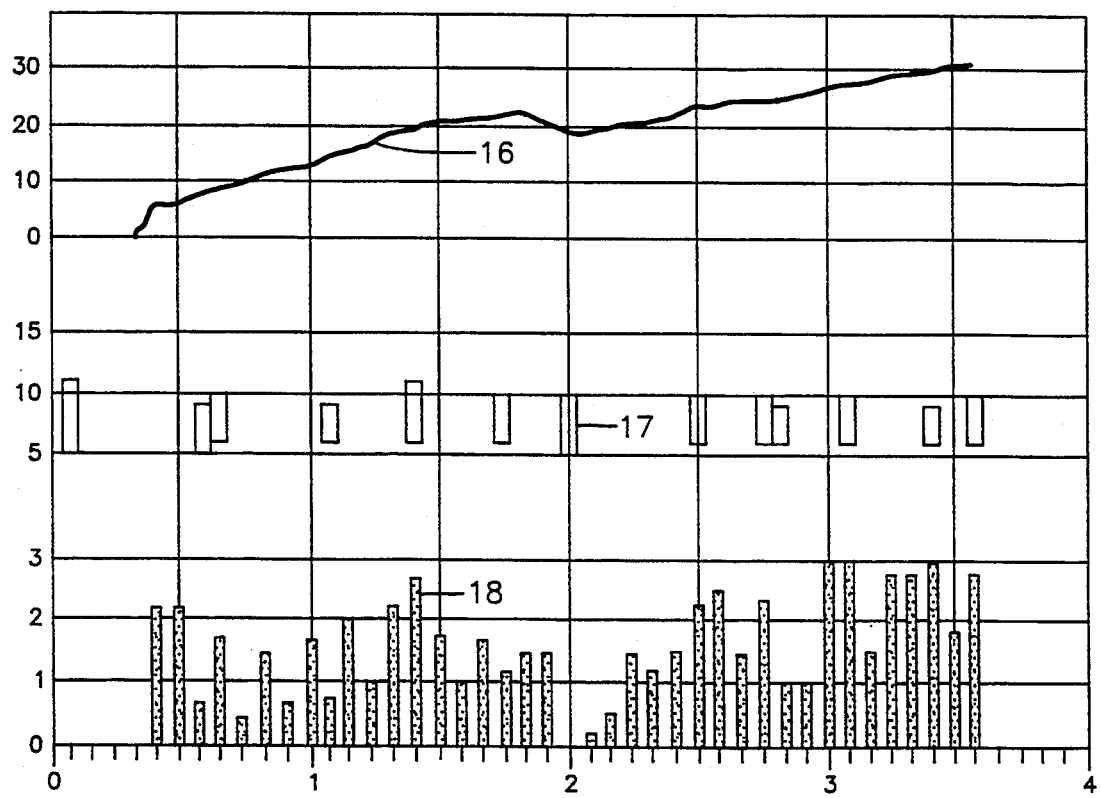

FIG. 5 shows the comparative change in the circulating blood volume of the patient and of his arterial blood pressure.

Figure 6A:
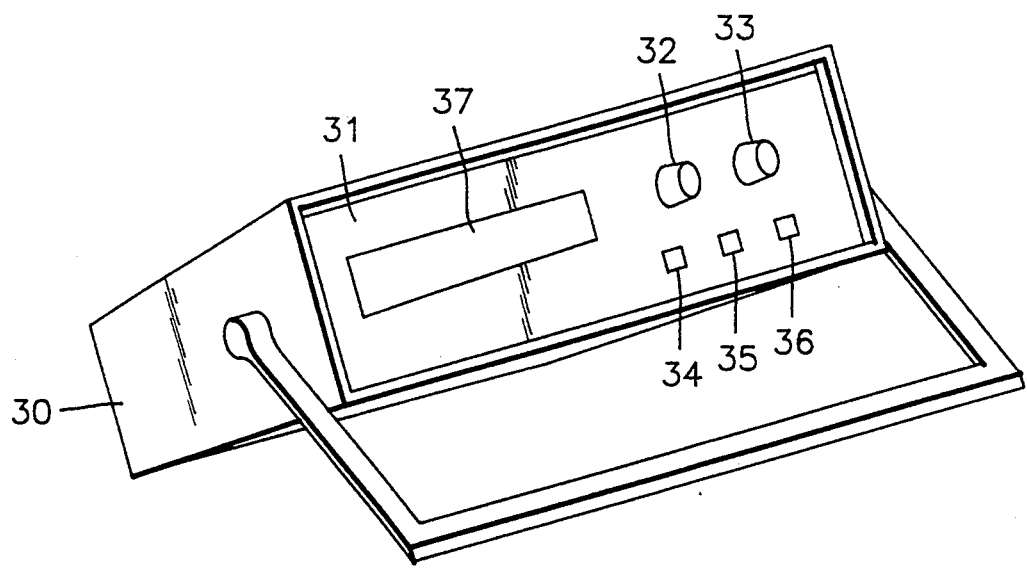
Figure 6B:
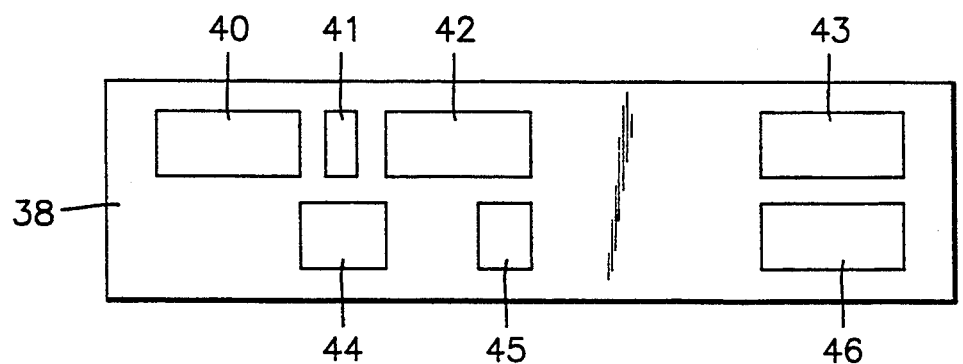
Figure 6C:
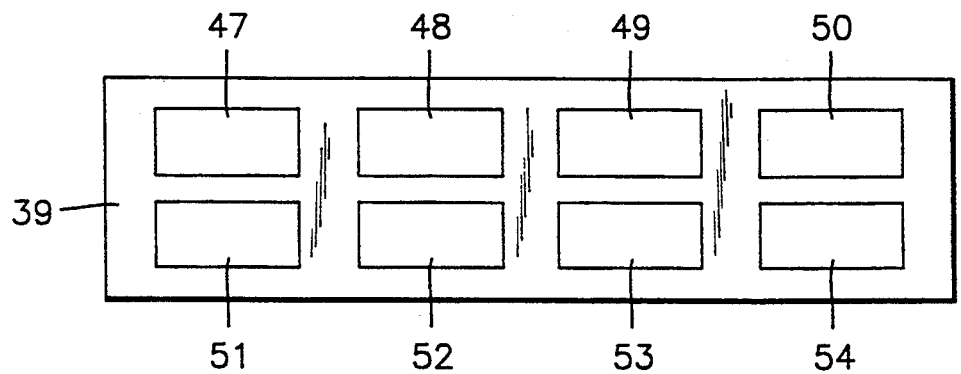

FIG. 6 shows an embodiment of the apparatus of the invention.

DESCRIPTION OF THE PREFERRED EMBODIMENT

Figure 1:
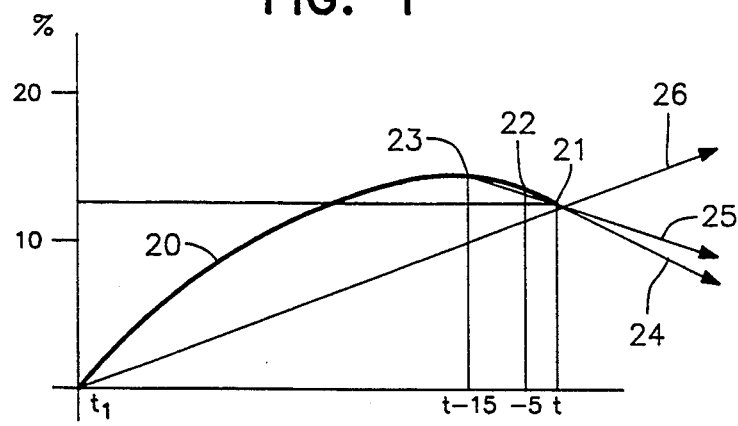
FIG. 1 shows the change in the relative variation of the plasma volume in time.

In FIG. 1, the change in the relative variation of the haematocrit is shown as it can be determined from the measurement taken in real time on the blood of a patient during a haemodialysis session.

The variation in the haematocrit can be determined for example by simple colorimetric measurement or, according to the preferred embodiment of the invention, by impedancemetry. A colorimetric measurement can also be combined with a measurement by impedance meter.

The function of the haematocrit considered according to the invention may be of different types. We now consider the relative variation in the plasma volume:

$$\frac{VP_o - VP}{VP_o} = -\frac{\Delta VP}{VP_o} (t)$$

In FIG. 1, the time (in min) is on the X-axis and, on the Y-axis, the value:

$$\frac{-\Delta VP}{VP_o} \times 100$$

which is, in percentage, the relative variation of the plasma volume from time $t_0$ to time t. Curve 20 can be obtained from measurements taken by the apparatus of the invention.

At a given time t, three values of:

$$\frac{-\Delta VP}{VP_o}$$

are considered, the value at time t (point 21 on the curve), the value at the time preceding it by 5 min (point 22), and the value measured at the time preceding it by 15 min (point 23). The measurement principle of the invention consists in comparing the change in the slope of the curve 20 over the short period (5 min here) materialized by line 24, against that the of slope on the medium period (15 min here) materialized by line 25, and against the long period (from the start of dialysis), line 26.

Colorimetric methods used to monitor the red cell count of the blood are well known. The method preferred here is that in which the light source and detector are positioned on the same side of the cell where the blood circulates. This allows a measurement of the backscattered light and is thus less sensitive to artefacts. However, the electrical method for indirect evaluation of the haematocrit from a measurement of the blood impedance is the most commonly practised and the easiest to implement. This is the method that will be described in detail below.

Figure 2:
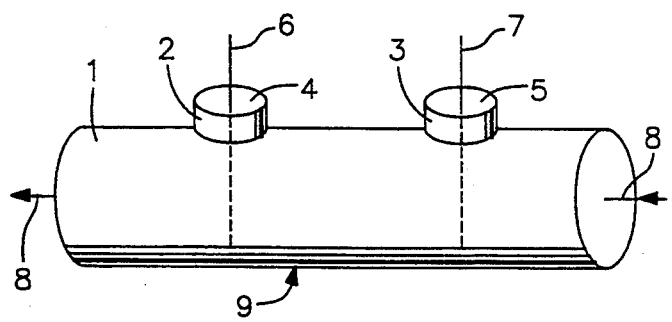
FIG. 2 shows the impedance measurement cell implanted in the external blood circuit.
Figure 3:
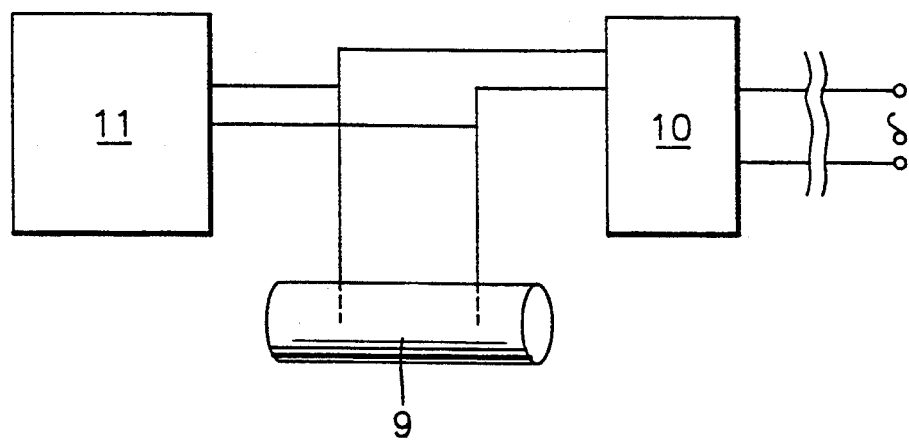
FIG. 3 shows the impedance measurement.

FIG. 2 shows a semi-rigid plastic tube 1 with a clearly-defined cross-sectional area, for example 20 mm². At two positions at a typical spacing of 70 mm, are positioned two caps 2,3 closed by an elastomer at 4,5 in which the electrodes 6,7 are inserted. These electrodes are, for example, two sterile needles introduced through the membranes 4,5, which close on them in a hermetically sealed manner. These membranes constitute the side walls of the tube 1 in which patient's blood 8 circulates. The overall assembly is sterile and preferably disposable. This measurement cell 9 is placed preferably at the inlet of the haemodialysis system. Thus the temperature of the cell remains approximately constant, and is barely lower than the patient's temperature. FIG. 3 shows the same cell 9 supplied by a constant-current generator 10. This current is sinusoidal with a frequency of 5 kHz. Thanks to the impedance meter 11, the measurement of the potential difference between electrodes 6,7 at a given time gives a measurement of the impedance Z of the blood at this time.

FIG. 3 shows the complete functional diagram of the measurement circuit. A protection circuit is shown at 12, designed to avoid any risk of direct connection between the a.c. power supply mains and the apparatus—especially its electrodes in contact with the patient's blood. At 13 is shown the low-voltage power supply at a frequency of 5 kHz, and at 10 the constant-current generator which supplies the electrodes, while the impedance meter 11 calculates the impedance between the electrodes 6,7 from the drop in the a.c. voltage measured between them, and its outlet. The signal obtained is proportional to the instantaneous impedance Z. The calculator 14 takes the readings of these measurements at a rate of n/s, for example 5. The calculator 14, which is part of a microprocessor, first performs a smoothing of the instantaneous measurements, calculates the mean of Z over p seconds, for example over 5 seconds. In the example, the measurement is hence averaged over 25 elementary measurements. This gives a value Zm. This is the measurement that serves to monitor the change in impedance over time.

The impedance Z of the blood measured at 5 kHz (which is the equivalent of the electrical resistance measured in direct current) is proportional to the red cell count in the blood and hence to the haematocrit (ratio of the volume occupied by the red blood cells to the whole blood volume).

The apparatus of the invention is turned on about 5 min after the start of the haemodialysis session. It determines a first value of $Z_0$. This value, thanks to a previous calibration, allows a calculation of the corresponding haematocrit. An estimation of the patient's whole blood volume made by the practitioner helps to determine the initial plasma volume $VP_0$ (plasma volume+volume of red blood cells=whole blood volume).

Starting at time $t_0$ of the start of measurement, the impedance Z is measured permanently and stored. The useful values for monitoring haemodialysis are taken from memory as required.

Two quantities are useful for this monitoring, the relative variation of the haematocrit (which is approximately equal to the relative variation of the plasma volume, to within a sign), and the level of this haematocrit (or of this plasma volume) which is proportional to the impedance. Each of these two quantities is analyzed and allows the independent evaluation of an indicator of the progress of haemodialysis. The combination of these two indicators helps to determine an alert level.

The method of the invention is implemented at regular intervals during haemodialysis session, for example every 5 min. FIG. 1 shows the quantities that are calculated at each implementation: these are the slope over the short period PCD represented by line 24, the slope over the medium period (PMD(line 25)) and the slope over the long period (PLD), for the first haemodialysis indicator (slope indicator IP). On the other hand, to calculate the threshold indicator IS, the value on the X-axis of point 21 itself is used.

The slope indicator IP is the sum of three quantities. The first, $A_1$, depends on the short-term slope PCD, the second $A_2$ depends on the medium-term slope PMD, and the third, $A_3$, is associated with the very long-term slope (PLD) (line 26 in FIG. 1). These three slopes are expressed as percentages of the variation of the plasma volume related to one minute and given the negative sign.

Term $A_3$ is always the same function of the slope over a long period:

$$A_3 = \left| \frac{PLD}{10} \right|$$

(absolute value rounded off to the closest integer).

The other two terms, $A_1$ and $A_2$, are composed of two parts, one which depends only on the slope and the second which results from a comparison of the slope with the slope over the immediately longer period.

The expression of $A_2$ is thus:

$$A_2 = \left| \frac{PMD}{15} \right| + \text{constant}$$

where $|PMD/15|$ is the absolute value rounded off to the nearest integer, this constant being $+1$ if:

PMD<PLD−1 and −1 if:

PMD>PLD+4

Similarly, the expression of $A_1$ is:

$$A_1 = \left| \frac{PCD}{20} \right| + \text{constant}$$

where $|PCD/20|$ is the absolute value rounded off to the nearest integer. The constant is equal to $+2$ if:

PCD<PMD−4 and equal to −2 if:

PCD>PMD+4

This shows that the slope indicator IP is always expressed by a whole number, positive or negative. The microprocessor of the apparatus is designed to keep IP within the range $-9/+9$ (the values outside this range are in fact always due to artefacts, as proved by experience).

The threshold indicator IS is expressed by:

$$\frac{\left( \frac{-\Delta VP}{VP_o} \times 100 \right)^2}{100}$$

This value is also rounded off to the nearest integer. For the same reasons as above, it is limited to the range, $0/+9$.

The alarm level (NA) is equal to the addition of the preceding two indicators:

$NA = IP + IS$ $-9 < NA < +18$

The positive values are the only ones that trigger the alarm.

Depending on the characteristics of the patients (corpulence, general condition etc), a limit is set for NA, which is either 4, 8 or 12. The apparatus is constructed so that, if the limit set is exceeded, a sound alarm is triggered.

As shown above, IS by itself does not allow the prediction of incidents in the progress of dialysis. On the other hand, IP by itself cold give indications that can be used directly. Its combination with IS offers the advantage of allowing an even finer analysis, and hence an even better prediction.

In the event that the haematocrit is determined by impedance measurement, the drawback of the method could be that the variation in impedance may result either from the variation in circulating blood volume, or from the variation in the concentration of electrolytes in the plasma, particularly sodium, but the latter variations are slow and have little effect in the comparison of the slopes over short periods.

The apparatus of the invention is shown in FIG. 6. This is a model with indication of plasma volumes VP. Shown at 30 is the case, on the front of 31 of which the different components useful for the measurement are placed. These include the four-way mode selector 32, the three-way alarm selector 33, the push-button 34 for selection of the screen pages, the push-button 35 to start the measurement cycle, and the alarm switch 36.

Shown at 37 is the LCD screen. This screen allows the display, as selected (push-button 34) of one of the two pages, page 1 (38) or page 2 (39). The following are displayed on page 1:
- at 40, the initial impedance in k (time $t_0$),
- at 41, the operating incident indicator,
- at 42, impedance at time t,
- at 43, PCD at time t,
- at 44, value of IP, the slope indicator,
- at 45, value of IS, the threshold indicator,
- at 46, the value of the plasma volume VP at time t.

If page 2 is selected, it shows the following:
- at 47, the long period slope (PLD) from origin $t_0$,
- at 48, PCD at $t-10$ min,
- at 49, PCD at $t-5$ min,
- at 50, PCD at time t (as at 43, page 1),
- at 51, initial plasma volume $VP_o$ (in ml),
- at 52, absolute variation in VP at $t-10$ min,
- at 53, absolute variation in VP at $t-5$ min,
- at 54, absolute variation in VP at t (as at 45).

All the indications of the apparatus in FIG. 6 are in plasma volumes. This is a quantity that is easy to use by the practitioner. The value of the plasma volume is determined, as we have shown, from the measured value of the haematocrit, which is itself determined from an impedance measurement or a colorimetric measurement, or by any other method which allows the determination of the red cell count in the patient's blood.

A measurement is taken as follows.

The apparatus is switched on.

The electrodes are connected. Immediately, the impedance measurement taken every 5 s is displayed at 42.

Mode selector 32 is used to select either manual mode (impedance measurement only) or one of the three positions of automatic mode $A_1$, $A_2$ or $A_3$:
- $A_1$ corresponds to a patient with low corpulence (assumed blood rate 3500 ml),
- $A_2$ medium corpulence (4000 ml),
- $A_3$ high corpulence (4500 ml).

The alarm selector 33 is used to select the level for the sum (IS+IP) for which the alarm must be triggered. In the case described previously, three levels were indicated, 4, 8 and 12 (high, medium and low sensitivity respectively).

As soon as the dialysis parameters are stabilized, generally 5 min after the start, push-button 35 is pressed.

If the instrument is in automatic mode (position $A_1$, $A_2$ or $A_3$ of push-button 32) the measurements are taken as follows:
- from 0 to 10 min: observation of the weighted starting value of the impedance,
- at the 10th minute: calculation and display of $Z_o$ (40) and of the initial plasma volume (51),
- at the 15th minute: calculation and display of the first variation in plasma volume (46 and 54) and short-term slope PCD (43 and 50) which is exceptionally the same as PLD (47),
- then, every 5 min, calculation and display of all the values, particularly IP and IS, and triggering of the alarm if: $IP + IS \geq$ alarm threshold (as selected at 33).

The following example compares the variation in the measurement of the extra-corporeal haematocrit or that of its inverse corollary, the circulating blood volume, with the change in the arterial blood pressure of the patient. It shows that the method of the invention serves to predict problems in the patient at least 15 min before they occur, and thus gives the practitioner the possibility of avoiding them.

The example is illustrated in FIG. 5. On the X-axis is the time expressed in hours. The Y-axis, in its median portion 17, shows the values of the arterial blood pressures expressed in cm of mercury and, in its upper portion 16, the relative variation of the plasma volume $-\Delta VP/VP$ expressed in %.

This is a quantity proportional to the impedance Zm at the same time, the value that has served to determine the alert levels shown at the bottom of the diagram at 18. These alert levels, equal to IP+IS, range between 0 and 12. As shown above, the thresholds are set at 4, 8 and 12 respectively.

In the figure, it is possible to observe the correspondence between the haematocrit (in this case the plasma volume), the alarm level and the arterial blood pressure. One may observe in particular that, as the slope of the curve of the haematocrit rises, the alarm threshold increases, and that, shortly afterward, the patient's blood pressure decreases. Thus, at 25 min, the slope rises sharply, the alarm level exceeds threshold No. 2 (value of 9). It is 15 min later that the pressure has fallen. Similarly, at 2 h 35 min, level 10 has been reached and it has been followed by an improvement, and then again by a disturbing level at 2 h 45 min, itself followed 5 min later by a drop in blood pressure. It must be pointed out that the experiment was conducted without the action of the practitioner, whereas, normally, as soon as the first alarm is triggered, he will have taken action, either by slowing down the ultrafiltration, or by the injection of solutes which induce an effect of plasma expansion (osmotic effect).

In FIG. 5, no measurement has been taken despite the first alarms due to the slope alone. This is why subsequently the effect of the haematocrit level has been determining on the subsequent alarms.

The method for monitoring the haematocrit of the patient's blood during haemodialysis described above essentially used the impedance measurement. In fact, electrical measurements are easy to take and to computerize. However, any method that allows the monitoring of the change in a quantity proportional to the haematocrit or to the circulating blood volume is suitable for implementing the invention. This also applies to optical methods such as colorimetry, for example, which allows a very accurate monitoring of the red cell count of the blood and hence of the haematocrit.

In comparison with the prior art, the invention offers the advantage of allowing very early detection of hypovolaemia, long before the physical manifestation, the arterial blood pressure, which was hitherto easier to detect. In the case of patients with atypical behavior, it makes it possible, from the first dialysis following a dialysis where an incident has occurred, to predict any new incident very safely. The implementation of the technique of the invention is simple, not traumatizing for the patient because its device is easily incorporated with the artificial kidney itself. The results of the method of the invention have also proved to be independent of the variations in natraemia (sodium content in the blood). The handling of the apparatus is particularly simple and requires only a short learning period for the practitioner who wants to employ it. Moreover, for risk patients or for research purposes, it is always possible to monitor the progress of dialysis in real time. Similarly, it is possible to record and store the data by data processing means and accordingly to allow both the monitoring of the change in a patient, as well as studies of a scientific character (and possibly statistical) of greater scope. The method is simple from the electrical/electronics standpoint, the production cost of each device is thus limited, and it is possible to provide each haemodialysis center with the necessary number of units.

What we claim is:

1. A process for monitoring the progress of hemodialysis by extra-corporal measurement of hematocrit, comprising the steps of:
   a) continuously measuring values representative of the hematocrit,
   b) continuously determining variations of these values over a short time period, over a medium time period and over a long time period, and normalizing the values with respect to a unique time base, obtaining thus normalized parameters PCD, PMD, and PLD, representative, respectively, of the variations of the hematocrit value measured over a short time period, over a medium time period, and over a long time period,
   c) calculating a slope indicator value from the parameters PCD, PMD, and PLD in such a manner that the slope indicator increases inversely proportionally to an increase of the hematocrit,
   d) determining an alarm indicator value by combining the slope indicator value with a threshold indicator value which depends on the specific hematocrit, and
   e) initiating action to prevent cardiovascular collapse in response to reaching the alarm indicator value.

2. A process according to claim 1, wherein the slope indicator value increases when variation of the value representative of the hematocrit over a short time period is less than the corresponding variation over a medium time period, and the slope indicator value decreases when the variation of the value representative of the hematocrit over the short time period is higher than the corresponding variation during the medium time period.

3. A process according to claim 1, wherein the slope indicator value increases when the variation of the value representative of the hematocrit over a medium time period is less than the corresponding variation over a long time period, and the slope indicator value decreases when the variation of the value representative of the hematocrit over the medium time period is higher than the corresponding variation over the long time period.

4. A process according to claim 1, wherein the long time period is defined as the total time elapsed since the beginning of the hemodialysis, the medium time period is in the order of 15 minutes and the short time period is in the order of 5 minutes.

5. A process according to claim 4, wherein the slope indicator value is obtained by combining parameters representative of the short time period variation, the medium time period variation, and the long time variation of the hematocrit value in such a way that the long time parameter has double weight with respect to the short time period parameter and one and a half times weight with respect to the medium period parameter.

6. A process according to claim 5, wherein the slope indicator value is obtained by combining the short time period, medium time period, and long time period parameters in such a way that the variation of the short time period parameter with respect to that of the medium time period parameter has approximately double weight compared to the corresponding variation of the medium time parameter with respect to that of the long time period parameter.

7. A process according to claim 1, wherein the threshold indicator value is proportional to the square of the variation of hematocrit since the beginning of the hemodialysis.

8. A process according to claim 7, wherein the alarm indicator value is the sum of the slope indicator value and the threshold indicator value.

9. A process according to claim 1, wherein the hematocrit value is obtained by a measurement of blood impedance.

10. A process according to claim 9, wherein the impedance measurement results from averaged samples taken at a frequency of about 5 kHz.

11. A process according to claim 1 wherein said action comprises slowing down ultrafiltration.

12. A process according to claim 1 wherein said action comprises injection of solutes which induce an effect of plasma expansion.

13. Apparatus for monitoring the progress of haemodialysis by extra-corporeal measurement of the blood impedance comprising a measurement cell designed to be placed in a hemodialysis circuit, a constant-current generator, an impedance meter, said measurement cell comprising a semi-rigid tube provided with two openings closed by caps, two electrodes passing through said caps and each connected to the current source, and also connected to the impedance meter, wherein it comprises a calculator receiving the signal generated by the impedance meter and actuating an indicator of the progress of haemodialysis, in accordance with the process as claimed in claim 1.

14. Apparatus as claimed in claim 13, wherein the current source is supplied from the main power supply by a protection circuit.

15. Apparatus as claimed in claim 13, wherein the measurement cell is placed at the inlet of the hemodialysis device.

16. Apparatus as claimed in claim 13, wherein the current generator supplies a current with a frequency of approximately 5 kHz.

17. Apparatus for monitoring the progress of haemodialysis by extra-corporeal measurement of the blood impedance comprising a measurement cell designed to be placed in a hemodialysis circuit, a constant-current generator, an impedance meter, said measurement cell comprising a semi-rigid tube provided with two openings closed by caps, two electrodes passing through said caps and each connected to the current source, and also connected to the impedance meter, wherein it comprises a calculator receiving the signal generated by the impedance meter and actuating an indicator of the progress of hemodialysis, in accordance with the process as claimed in claim 1, wherein the current source is supplied from the main power supply by a protection circuit, wherein the measurement cell is placed at the inlet of the hemodialysis device, wherein the current generator supplies a current with a frequency of approximately 5 kHz.

18. Apparatus as claimed in claim 13, which comprises means for:
a) continuously measuring values representative of the hematocrit,
b) continuously determining variations of these values over a short time period, over a medium time period and over a long time period, and normalizing the values with respect to a unique time base, obtaining thus normalized parameters PCD, PMD, and PLD, representative, respectively, of the variations of the hematocrit value measured over a short time period, over a medium time period, and over a long time period,
c) calculating a slope indicator value from the parameters PCD, PMD, and PLD in such a manner that the slope indicator increases inversely proportionally to an increase of the hematocrit, and
d) determining an alarm indicator value by combining the slope indicator value with a threshold indicator value which depends on the specific hematocrit.

* * * * *